(12) United States Patent
Ganus

(10) Patent No.: US 9,349,492 B1
(45) Date of Patent: May 24, 2016

(54) RADIATION SHIELDING SUSPENSION DEVICE

(71) Applicant: Mantis Technologie, LLC, Lady Lake, FL (US)

(72) Inventor: Michael E Ganus, Mount Dora, FL (US)

(73) Assignee: Mantis Technologie, LLC, Lady Lake, FL (US)

( * ) Notice: Subject to any disclaimer, the term of this patent is extended or adjusted under 35 U.S.C. 154(b) by 0 days.

(21) Appl. No.: 14/719,729

(22) Filed: May 22, 2015

Related U.S. Application Data

(60) Provisional application No. 62/096,225, filed on Dec. 23, 2014.

(51) Int. Cl.
| | |
|---|---|
| *G21F 3/00* | (2006.01) |
| *G21F 3/03* | (2006.01) |
| *F16M 11/20* | (2006.01) |
| *F16M 11/42* | (2006.01) |
| *F16M 11/04* | (2006.01) |
| *F16B 1/00* | (2006.01) |

(52) U.S. Cl.
CPC ... *G21F 3/03* (2013.01); *F16B 1/00* (2013.01); *F16M 11/04* (2013.01); *F16M 11/2035* (2013.01); *F16M 11/42* (2013.01); *F16B 2001/0028* (2013.01)

(58) Field of Classification Search
USPC ........... 250/505.1, 506.1, 515.1, 516.1, 517.1
See application file for complete search history.

(56) References Cited

U.S. PATENT DOCUMENTS

| | | | |
|---|---|---|---|
| 7,973,299 | B2 | 7/2011 | Rees |
| 2006/0189453 | A1 | 8/2006 | LeBlond |
| 2007/0004567 | A1 | 1/2007 | Shetty et al. |
| 2007/0138415 | A1* | 6/2007 | Rees .................. G21F 3/02 250/516.1 |
| 2009/0256044 | A1 | 10/2009 | Miller et al. |
| 2010/0107320 | A1 | 5/2010 | Rees |
| 2011/0253914 | A1 | 10/2011 | Rees |
| 2013/0270462 | A1* | 10/2013 | Beck ................ A61B 6/4423 250/516.1 |
| 2013/0306824 | A1 | 11/2013 | Miller et al. |

FOREIGN PATENT DOCUMENTS

DE    2934955 A1    8/1979

* cited by examiner

*Primary Examiner* — Nicole Ippolito

(74) *Attorney, Agent, or Firm* — Mitchell J. Mehlman, Esq.

(57) ABSTRACT

A radiation shielding suspension device comprising a support member, a vertical member, a swing arm, an attachment member, a balancer, a spreader bar, and a plurality of straps, being attachable a radiation shielding garment, such as a lead apron is provided. An operator can attach straps to a radiation shielding garment thus offsetting the weight of the garment and providing the operator unbiased mobility along a transverse axis and around a rotational axis.

20 Claims, 7 Drawing Sheets

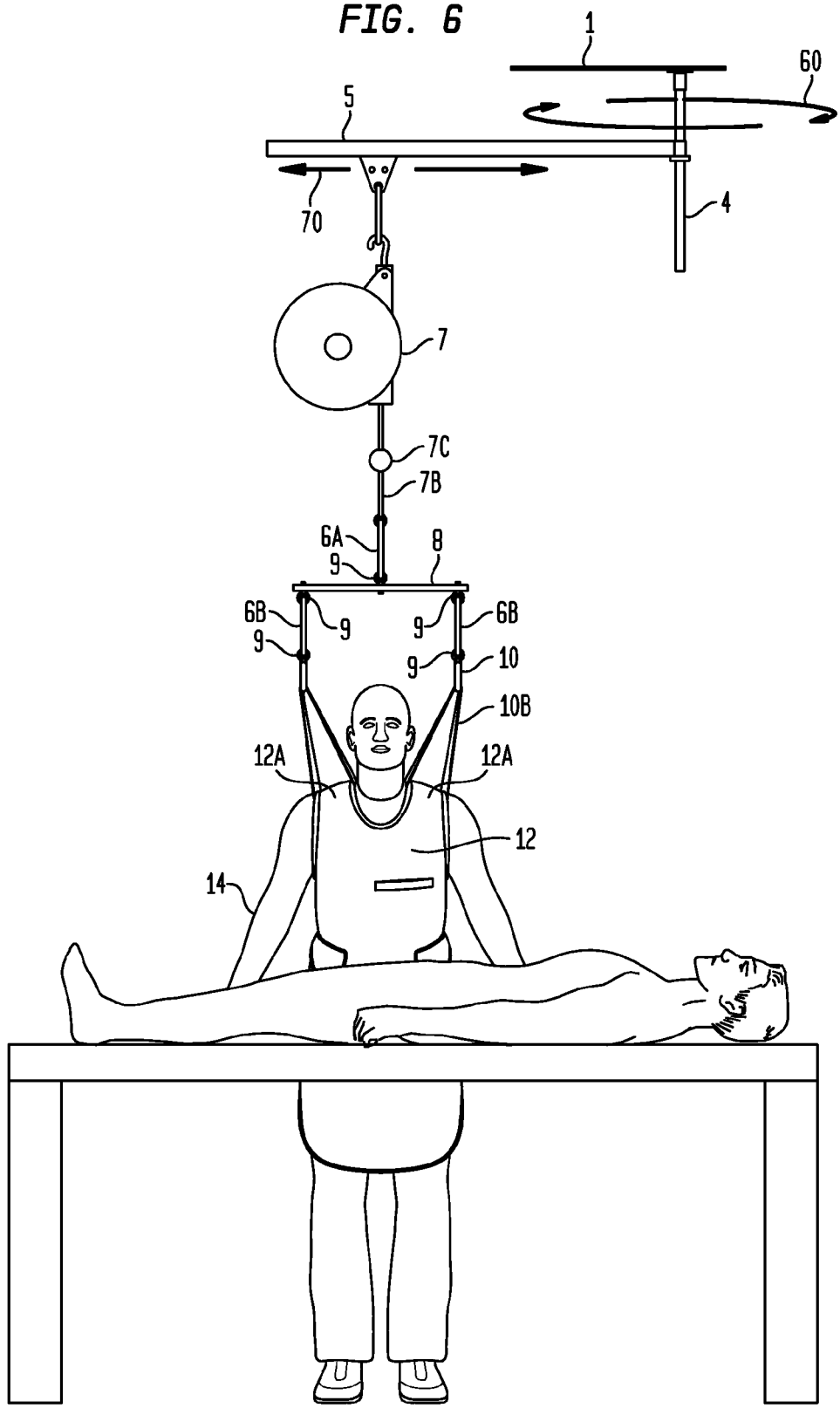

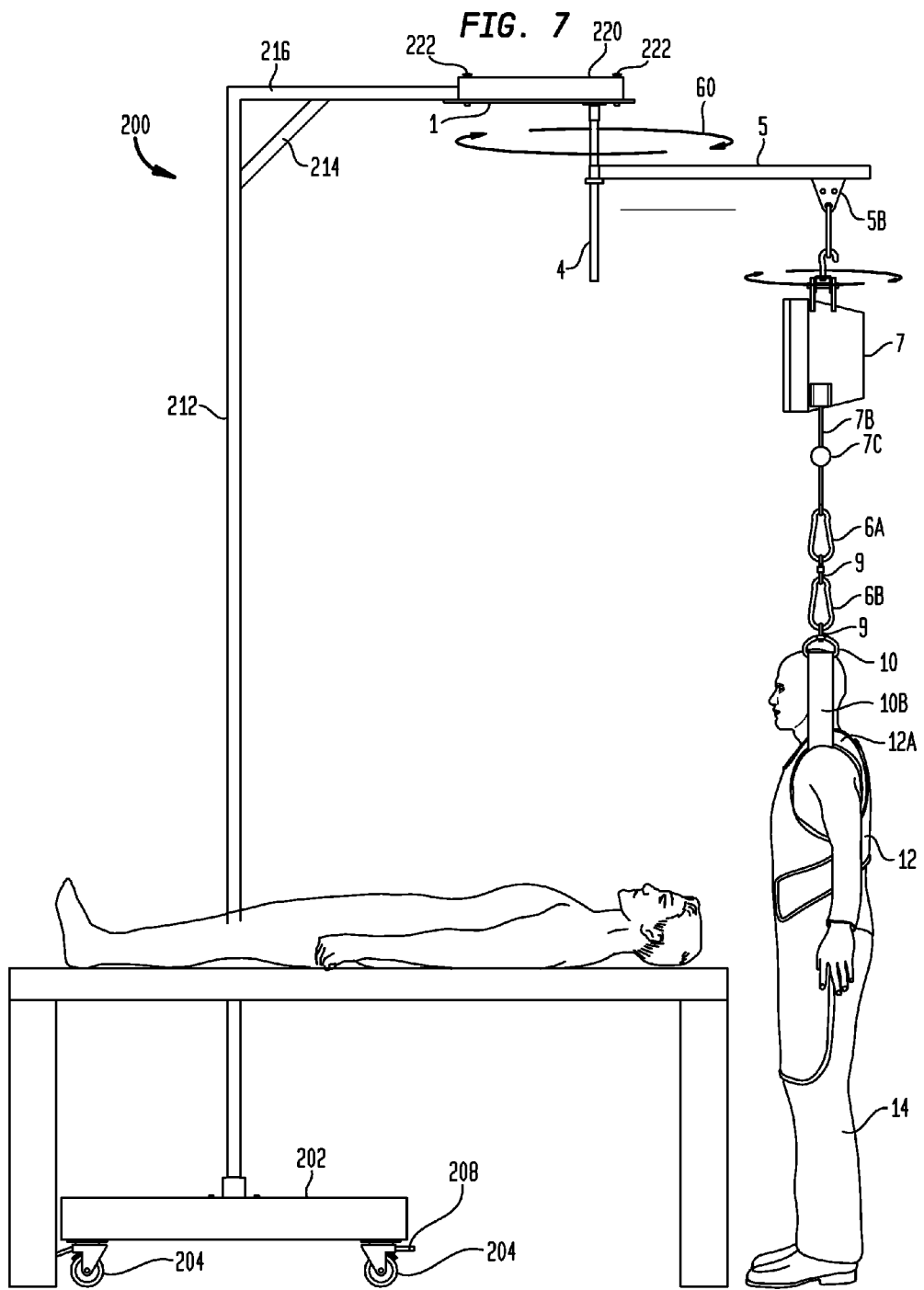

RADIATION SHIELDING SUSPENSION DEVICE

CROSS-REFERENCES

This application claims the benefit of U.S. provisional application 62/096,225, filed Dec. 23, 2014, the contents of which is incorporated by reference in its entirety.

BACKGROUND

The invention as disclosed and described herein relates generally to suspension devices, and more particularly to devices for suspending medical equipment such as personal radiation shields or lead aprons worn by medical personnel in a medical environment.

Performance of medical procedures can be a physically demanding job, potentially creating discomfort and health issues for medical personnel. For example, a doctor performing a medical procedure can expose his body to radiation, such as X-rays, which are used to perform many medical diagnostic and therapeutic tests and procedures. In particular, cardiac catheterization procedures can expose doctors and other medical personnel to potentially dangerous X-rays.

To minimize exposure to radiation, medical personnel performing procedures having risk of X-ray exposure commonly wear personal protective garments containing radiation-absorbing materials, generally lead foil or other metals, which are worn in the fashion of a vest and apron.

Such garments can be uncomfortable, heavy and place significant stress on the operator's body, especially the spine, over the course of a working day which may be 8 hours or longer. This issue presents a significant health concern for medical operators in radiation environments, such as personnel in a cardiac catherization laboratory or orthopedic operating theater.

The effects of an operator wearing a heavy radiation shielding garment over an extended period of time is known to be associated with maladies of the cervical, thoracic or lumbar spine, knee problems, foot problems, and other musculoskeletal dysfunctions, which can result in disability, medical expenses, and decreased quality of life for the operator. Further, the use of such garments can impact the quality of patient care by placing undue physical stress on the operator.

Thus, there is a need for radiation shielding suspension devices for use in a medical environment. In one aspect, the suspension device allows an operator to wear a personal radiation protection garment by suspending the garment thereby offsetting the weight of the garment on the operator's body and eliminating stress on said operator's musculoskeletal system. Further, the device does not limit freedom of movement. In one aspect, the device allows for vertical, rotational, and axial or translational movement of the support mechanism.

Known systems include suspension systems such as, for example, the system described by U.S. Pat. No. 7,608,847, to Rees, the contents of which is hereby incorporated by reference in its entirety.

Thus, detailed explanations of the functioning of some of the components and method of such suspension systems are deemed unnecessary for understanding of the present invention by one of ordinary skill in the art, however the following description is instructive.

Cranes might be used to support a load up to 250 pounds, are often operated by workers without the aid of motorized assistance, since the crane's movable parts are light enough to be manipulated by hand. Different systems are employed to suspend the load from the cranes, including hoists, and balancers, such as tool balancers.

Tool balancers are also currently available and help to suspend tools in the workspace in a manner that provides ergonomic benefit for workers using them.

The tool balancer can generally be attached overhead the workspace, and reels out cable from which the tool is suspended. Adjustments may be made to provide a "zero gravity" balancing of the tool at the desired height, such that the worker may move the tool up or down within a working range without having to bear a significant portion of the tool's weight.

Different adjustment may cause the tool balancer to exert a stronger upward force such that the operator must apply a downward force on the tool to pull it down to the workspace, and the balancer will cause the tool to rise when the operator releases it.

Tool balancers may be of the spring or pneumatic variety, referring to the mechanism, which provides the force for its operation. A spring tool balancer, such as in the preferred embodiment of this invention, generally contains a coiled flat spring, similar to a clock spring, which is attached to a reel with a conical shape and serves as the platform for the winding of the cable. The conical shape provides a variable mechanical advantage, which offsets the variance of the force provided by the spring as it winds or unwinds. The result is a relatively constant force on the cable within a definable working range.

Safety concerns mainly involve falling objects, strength of the suspension device, strength of the cable, and operator falls. The balancer can be attached to the axial swing arm by its own hook and can include a safety chain. The suspension device is commercially available at specified maximum loads, which include a wide safety margin. The mounting of the suspension device will be done according to essential architectural and safety standards.

Detachment of the garment from the suspension device will require certain care. A cable stop will prevent the hanger from going higher than the set level. An operator can remove the garment without concern for sudden upward, uncontrolled motion of the balancer cable and hanger or spreader bar.

Alternatively, a weight, which is approximately equivalent to the weight of the garment, could be attached to the hanger prior to disengaging the garment. This will drop the garment and require it to be supported by the worker, who may then disengage it from the hanger. The weight will prevent any upward motion of the hanger in an uncontrolled manner. The next time the garment is attached, the weight could be removed after secure attachment of the garment is confirmed.

For most operation, the garment need not be detached from the cable. It could be left suspended and moved out of the way of other activities. Another alternative method would involve setting the force on the balancer to be slightly greater than the weight of the garment. Once removed from the body, the garment would then slowly and safely rise up until stopped by the cable stop. Upon next use, it could easily be pulled back down into position.

In the event of an operator fall, it is unlikely that the system will contribute to operator harm since the balancer cable is long enough to allow the operator to reach the floor. Any harm to the operator should be the same as if not attached to the cable, except perhaps for some beneficial effect of the upward force of the suspension system.

In the event that rapid detachment of the operator from the system is necessary due to emergency, this can be achieved by simple removal of the garment from the body without detachment from the system. The garment can be left hanging, and the suspended garment can be moved to the end of the runway, clear of the moving patient or stretcher.

Alternatively, quick release hook and loop shoulder straps, such as Velcro™ can be rapidly disconnected thereby allowing the operator to walk away wearing the garment without being encumbered.

While some known devices may work for their intended purpose, there is a need for improved suspension devices which have additional benefits, yet none of the shortcomings.

SUMMARY

In one aspect of the present invention, a radiation shielding suspension device can comprise a support member. The support member can include at least one aperture for mounting support member to a structure. A vertical member can be fixedly attached to the support member and be substantially perpendicular to the vertical member. A swing arm can be rotationally attached to the vertical member. The swing arm can include a stop for fixing the swing arm at a plurality of vertical positions on the vertical member. A channel can include an axial member. The axial member is able to translate along a length of the channel. An attachment member can be connected to the axial support member. A balancer can have a hook for connecting to the attachment member and a cable for attachment to a central support member. The cable can include a slidable stop for adjusting the cable to a plurality of vertical positions. A spreader bar can include a first support ring for attaching to the central support member, a second support ring for attaching to a first lateral support member and a third support ring for attaching to a second lateral support member. The first and second lateral support members each can be attached to a first and a second support ring. A plurality of straps can be attachable to the first and second support rings and to a radiation shielding garment. An operator can attach the plurality of straps to the radiation shielding garment whereby the weight of said radiation shielding garment is substantially offset thereby allowing the operator substantially unbiased mobility along the transverse axis of the swing arm channel and around the 360 degree rotational axis of the vertical member.

In one embodiment of this aspect the structure can comprise a support stand, wherein the support member can be mounted to the support stand.

In another embodiment, the support stand can be portable and can include a plurality of wheels.

In some embodiments, the support stand can further include a plurality of wheel locks.

In yet other embodiments, the support stand can include a base, a vertical support post, a horizontal support post, and a mounting pad for mounting said support member.

In some embodiments, the plurality of straps can include hook and loop type fasteners.

In one particular embodiment, the plurality of straps can be two straps, each strap being attachable to one of two shoulder areas of a radiation shielding garment.

In some embodiments of this aspect, the balancer can be a spring type tool balancer.

In yet other embodiments, the radiation shielding garment can be a lead apron having two shoulder areas for attachment to the straps.

In another aspect of the present invention, a radiation shielding suspension device comprises a support member. The support member can include at least one aperture for mounting the support member to a portable structure. A vertical member can be fixedly attached to the support member and can be substantially perpendicular to the vertical member. A swing arm can be rotationally attached to the vertical member. The swing arm can include a stop for fixing the swing arm at a plurality of vertical positions on the vertical member, and a channel. The channel can include an axial member which is able to translate along the length of the channel. An attachment member can be connected to the axial support member. A balancer can have a hook for connecting it to the attachment member and a cable for attaching it to a central support member. The cable can include a slidable stop for adjusting the cable to a plurality of vertical positions. A spreader bar can include a first support ring for attaching to the central support member, a second support ring for attaching to a first lateral support member and a third support ring for attaching to a second lateral support member. The first and second lateral support members can be attached to a first and a second support ring, respectively. A plurality of straps can be attachable to the first and second support rings and to a radiation shielding garment. An operator can attach the plurality of straps to the radiation shielding garment such that the weight of the radiation shielding garment is substantially offset thereby allowing the operator substantially unbiased (i.e. the weight of the garment being neutralized) mobility along a transverse axis of the swing arm channel and around the 360 degree rotational axis of the vertical member.

In some embodiments of this aspect, the portable structure can comprise a support stand. The support member can be mounted to the support stand.

In some embodiments, the portable structure can include a plurality of wheels.

In certain embodiments, the portable structure can include a plurality of wheel locks or locking jacks.

In some embodiments, a portable structure can include a base, a vertical support post, a horizontal support post, a support brace, and a mounting pad for mounting the support member.

In certain embodiments, the plurality of straps can comprise hook and loop fasteners.

In a particular embodiment, the plurality of straps can be two straps. The straps can each be attached to the shoulder areas of a radiation shielding garment.

In some embodiments, the balancer can be a spring type tool balancer.

In some embodiments, the radiation shielding garment can be a lead apron.

In another aspect of the present invention, a method of preventing injury to an operator while wearing a radiation shielding garment can comprise:

Attaching a suspension device to a structure. The device can include a support member having at least one aperture for mounting the support member to the structure. A vertical member can be fixedly attached to the support member and be substantially perpendicular to the vertical member. A swing arm can be rotationally attached to the vertical member. The swing arm can include a stop for fixing the swing arm at a plurality of vertical positions on the vertical member, and a channel. The channel can include an axial member which is able to translate along the length of the channel. An attachment member can be connected to the axial member. A balancer can include a hook for connecting to the attachment member and a cable for attachment to a central support member. The cable can include a slidable stop for adjusting the cable to a plurality of vertical positions. A spreader bar can include a first support ring for attaching to the central support member, a second support ring for attaching to a first lateral support member and a third support ring for attaching to a second lateral support member. The first and second lateral support members each can be attachable to a first and a second support ring. A plurality of straps can be attachable to the first and second support rings and to the radiation shielding garment; and b) attaching the plurality of straps to the radiation shielding garment whereby the weight of the radiation shielding garment is substantially offset thereby allowing the operator substantially unbiased mobility along the transverse axis of the swing arm channel and around the 360 degree rotational axis of the vertical member.

In one aspect of this method, the structure can be a portable structure.

BRIEF DESCRIPTION OF THE DRAWINGS

FIG. 6 depicts an isometric view of one embodiment of the present invention as used in a treatment medical environment.

FIG. 7 depicts an isometric view of a portable version of one embodiment of the present invention in a medical environment.

DESCRIPTION

Figure 1:
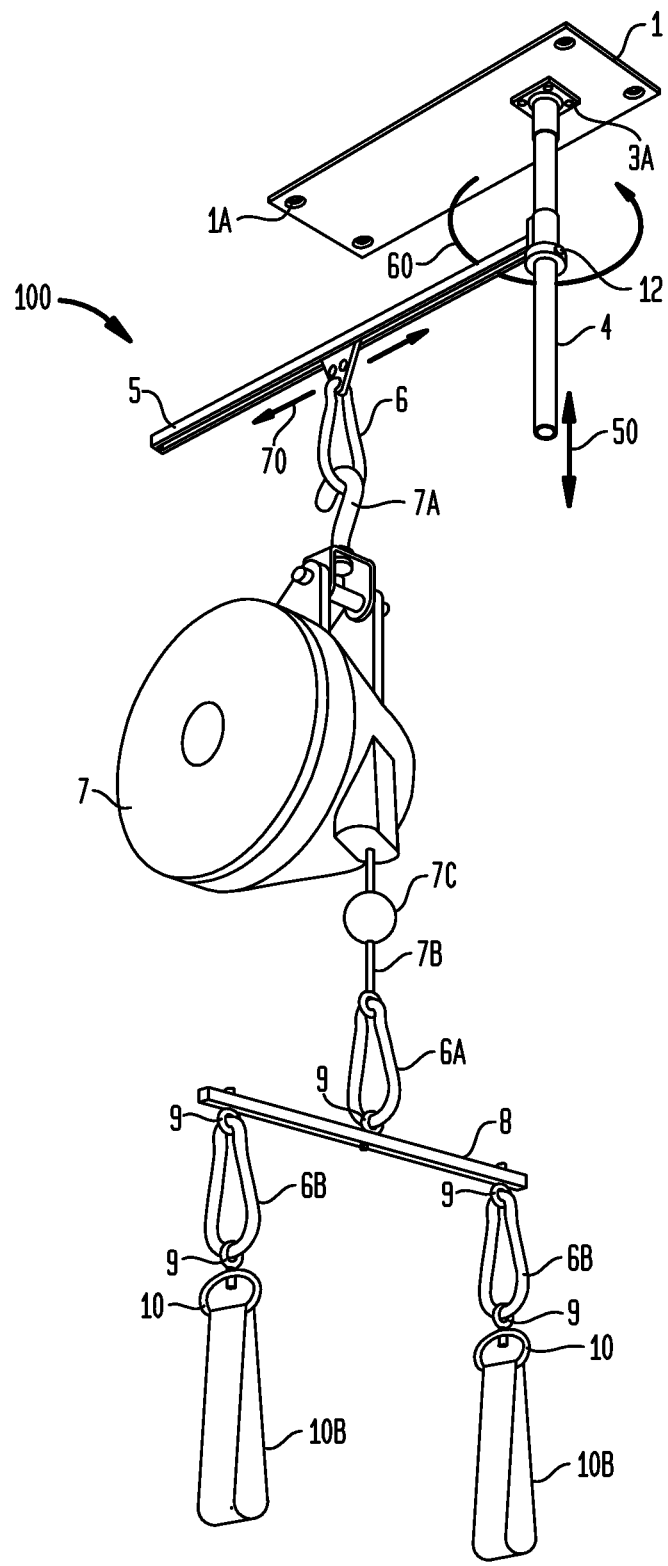
FIG. 1 depicts an isometric view of one embodiment of the present invention.
Figure 2:
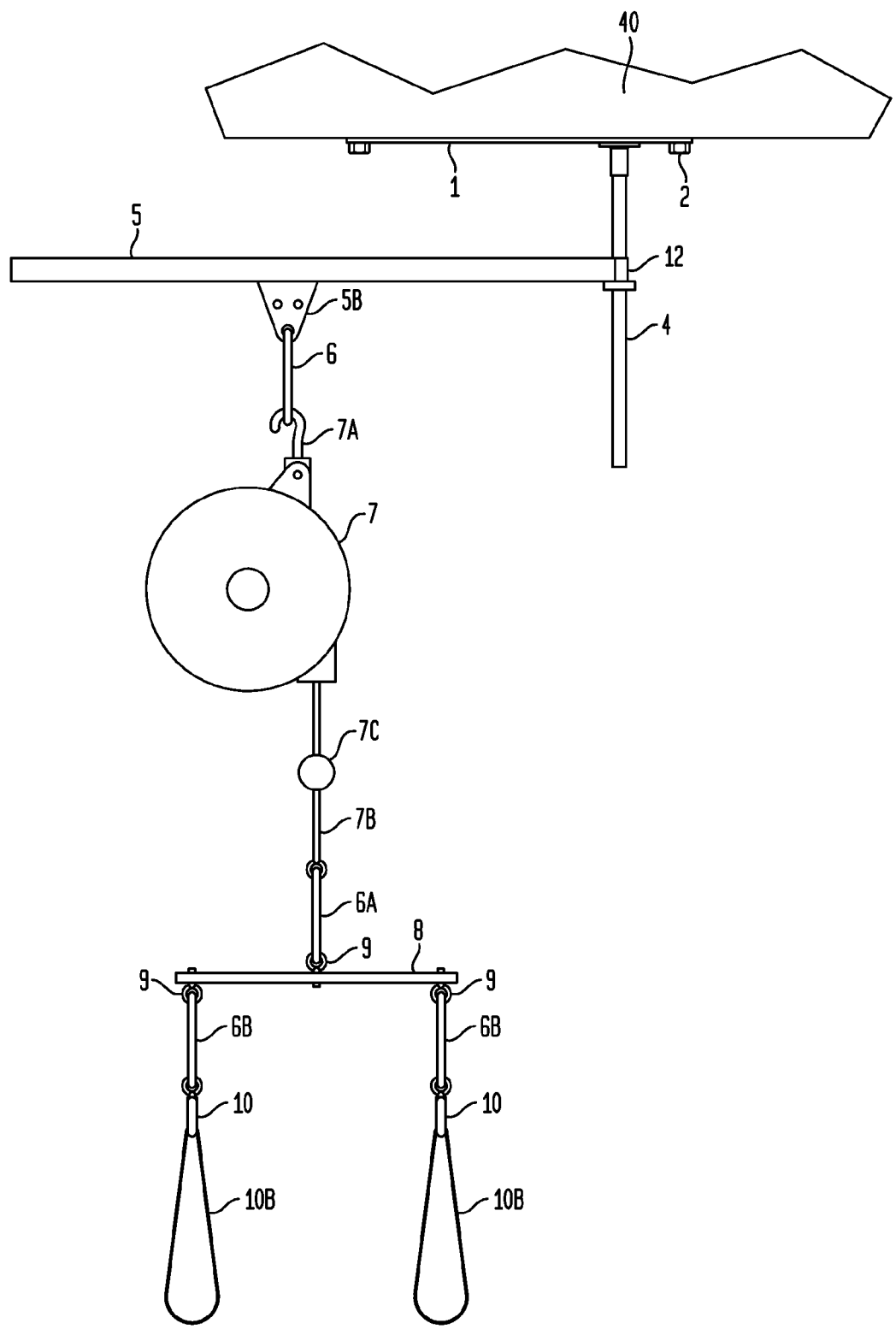
FIG. 2 depicts a side view of one embodiment of the present invention as mounted to a structure.
Figure 3:
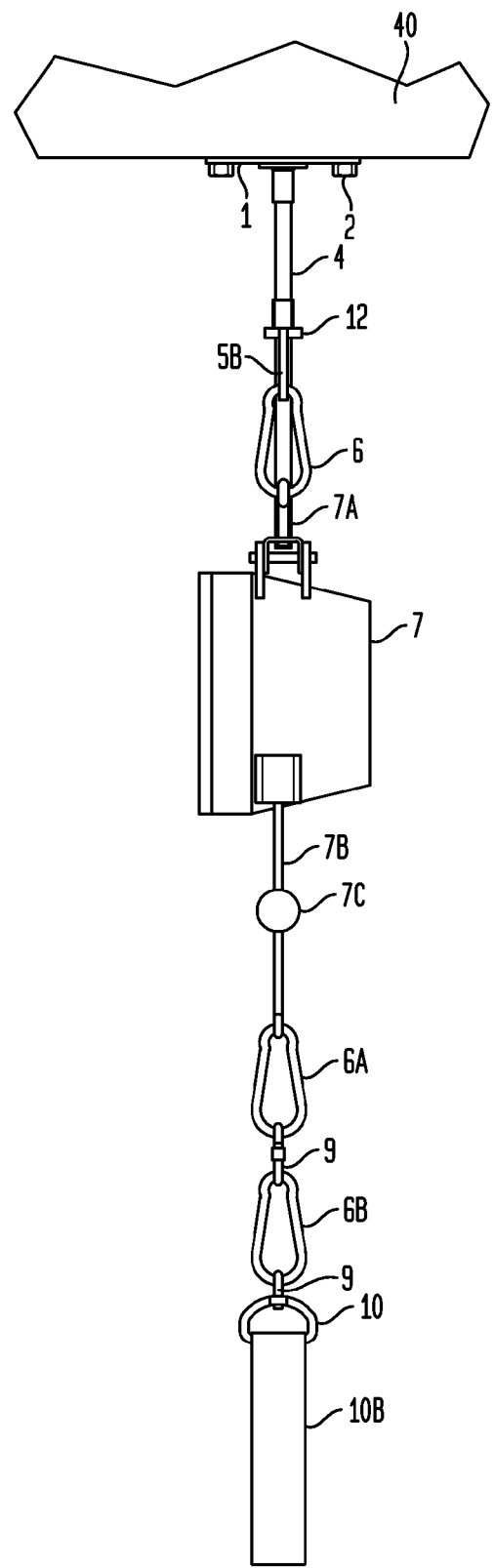
FIG. 3 depicts another isometric view of one embodiment of the present invention.
Figure 4:
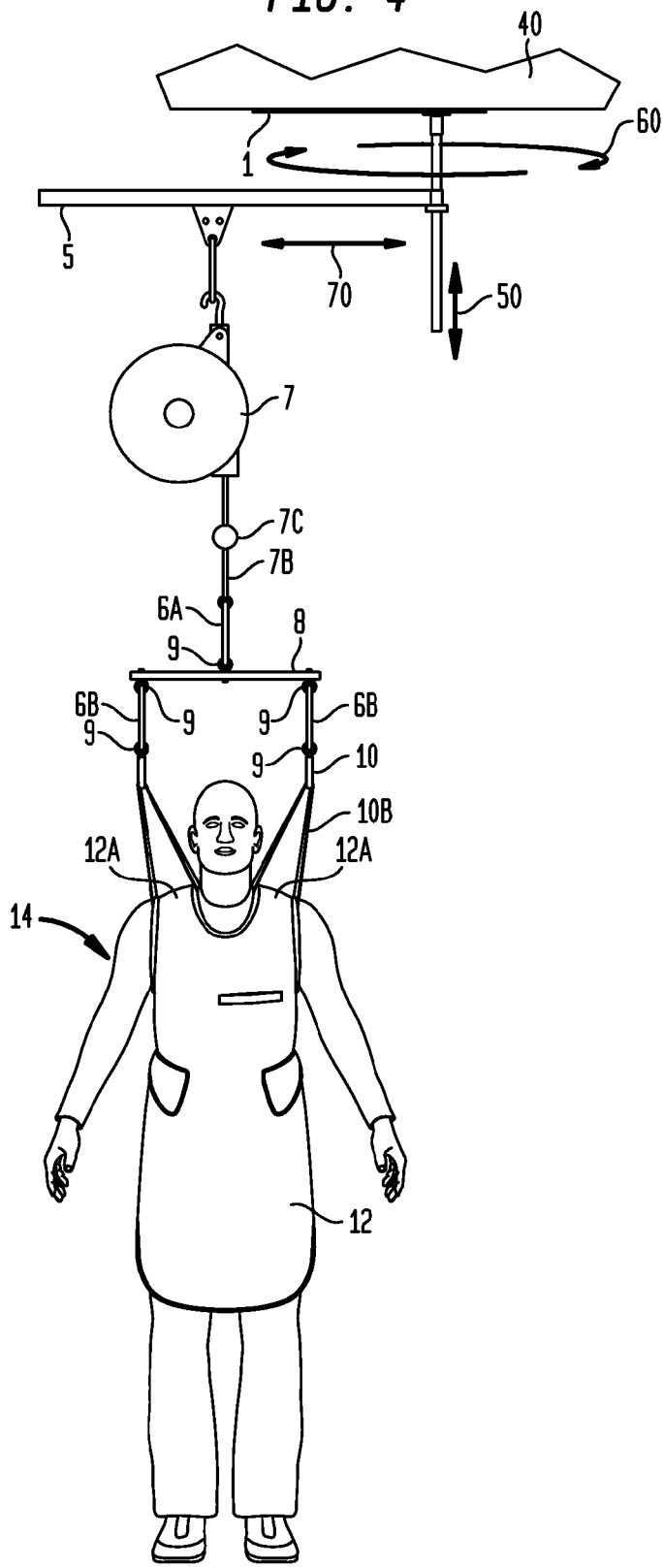
FIG. 4 depicts a front view of one embodiment of the present invention including a user.

In one embodiment of the invention as depicted in FIGS. 1-6, the device 100 comprises mounting plate 1. The plate 1 can include apertures 1A for attachment of the plate with fasteners 2 to a structural member (see for example 40 in FIG. 2), such as a beam in the ceiling of an operating room. The plate and fasteners are designed to support the load of the suspended device well within the margin of safety. In some embodiments, the mounting system can include one or more plates or a clamp which can attach to a structural member, such as a beam, or any other suitable support structure.

Vertical member 4 can be attached to plate 1 using flange 3A, by a threaded connection or by a welded connection. Member 4 can include screw stop 12 or other known means for providing a stop for swing arm 5 as discussed below. The swing arm can be fixed at a plurality of heights along the longitudinal axis 50 of member 4 thereby setting the height of the device.

In this embodiment, the device includes swing arm 5, which can be rotationally mounted to member 4 and can move about axis 60. The swing arm 5 can translate up (towards plate 1) or down (towards stop 12) thus allowing both vertical and rotational movement of the device.

Figure 5:
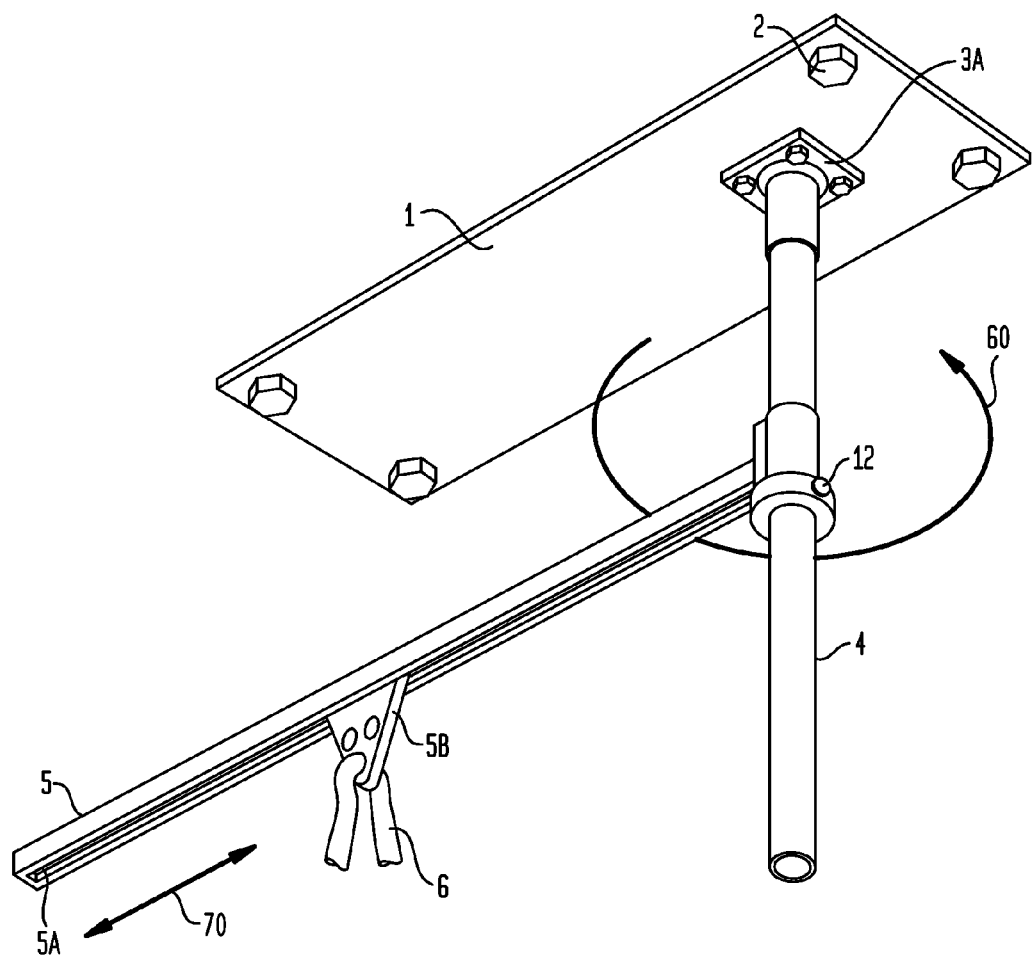
FIG. 5 depicts an isometric view of one embodiment of the present invention illustrating the rotational and translational axes.

As more clearly shown in FIG. 5, swing arm 5 includes a channel 5A which allows for axial translation of a sliding element 5B including attachment to carabiner 6. In this way, the device allows for vertical movement along axis 50, rotational movement around axis 60, and axial movement along axis 70 of the supported garments and users, thereby allowing operators freedom of motion in the operating room.

Balancer 7 can be attached to carabiner 6 using a hook 7A or other suitable mechanical attachment means. The balancer 7 includes a cable 7B for attachment to carabiner 6A and a stop 7C. In this way, the balancer cable can be set and fine-tuned to offset the weight of the garment or other load supported during use.

Carabiner 6A can be attached to spreader bar 8. The spreader bar 8 includes attachment rings 9 for caribiners 6A and 6B.

Support rings 10 can be attached to caribiners 6B and to hook and loop fastener straps 10B. The straps 10B can be removeably attached to the shoulder portions 12A of a lead apron 12 as worn by a user 14.

In this way, the balancer can be set to offset all or part of the weight of the radiation shielding garment or lead apron such that the operator can move about in an unfettered or unbiased way. That is, an unbiased movement is essentially neutral, meaning that the weight is offset by the device so that the operator does not feel the weight of the garment on his body. This allows the operator freedom of movement and prevents injury from the stress of wearing a heavy garment, such as a lead apron.

In some embodiments, the plate 1, can be mounted to a portable structure, such as a trolley having locking wheels or jacks (not shown). In these embodiments, the mounting plate can be attached to an overhead structure such as a plate or beam that can be moved to any area of interest, locked in place for use, unlocked and repositioned for use in the same or another area.

As shown in FIG. 7, a portable version of the invention 200 can include a portable support structure. In this embodiment, the mounting plate 1 can be attached to mounting pad 220. The plate and pad can be attached with fasteners 200 or other known fastening means. The pad 220 can be attached to the end of support arm 216 which is attached to post 212 and brace 214. The support structure can be attached using a flange and fasteners 222 to base 202. In certain embodiments, the base can include wheels 204 and wheel locks 208.

In this way, a radiation shielding suspension device, can be attached to the mounting pad of the portable structure rather than to a fixed structure such as a ceiling beam. Other known attachment means such as a plate or beams may be utilized. In this way, the device can be mounted and moved to any area, locking in place during use, and moved and repositioned to any suitable area if necessary. This portable configuration will provided additional advantages to the fixed configuration which will be recognized by a user or an ordinary person of skill in the art.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. A radiation shielding suspension device comprising:
   a support member, said support member including at least one aperture for mounting said support member to a structure;
   a vertical member, said vertical member being fixedly attached to said support member and being substantially perpendicular to said vertical member;
   a swing arm, said swing arm being rotationally attached to said vertical member, said swing arm including a stop for fixing said swing arm at a plurality of vertical positions on said vertical member, and a channel, said channel including an axial member, said axial member being able to translate along a length of said channel;
   an attachment member, said attachment member being connected to said axial support member;

a balancer, said balancer having a hook for connecting to said attachment member and a cable for attachment to a central support member, said cable including a slidable stop for adjusting said cable to a plurality of vertical positions;

a spreader bar, said spreader bar including a first support ring for attaching to said central support member, a second support ring for attaching to a first lateral support member and a third support ring for attaching to a second lateral support member, said first and second lateral support members each being attachable to a first and a second support ring; and a plurality of straps, said at plurality of straps being attachable to said first and second support rings and to a radiation shielding garment, wherein an operator can attach said plurality of straps to said radiation shielding garment whereby a weight of said radiation shielding garment is substantially offset thereby allowing said operator substantially unbiased mobility along a transverse axis of said swing arm channel and around a 360 degree rotational axis of said vertical member.

2. The radiation shielding suspension device of claim 1, wherein said structure comprises a support stand, wherein said support member is mounted to said support stand.

3. The radiation shielding suspension device of claim 2, wherein said support stand is portable and includes a plurality of wheels.

4. The radiation shielding suspension device of claim 3, further including a plurality of wheel locks.

5. The shielding suspension device of claim 2, wherein said support stand comprises a base, a vertical support post, a horizontal support post, and a mounting pad for mounting said support member.

6. The radiation shielding suspension device of claim 1, wherein said plurality of straps include hook and loop fasteners.

7. The radiation shielding suspension device of claim 1, wherein said plurality of straps is two straps, said two straps each being attachable to a shoulder area of said radiation shielding garment.

8. The radiation shielding suspension device of claim 1, wherein said balancer is a spring type tool balancer.

9. The radiation shielding suspension device of claim 1, wherein said radiation shielding garment is a lead apron.

10. A radiation shielding suspension device comprising:

a support member, said support member including at least one aperture for mounting said support member to a portable structure;

a vertical member, said vertical member being fixedly attached to said support member and being substantially perpendicular to said vertical member;

a swing arm, said swing arm being rotationally attached to said vertical member, said swing arm including a stop for fixing said swing arm at a plurality of vertical positions on said vertical member, and a channel, said channel including an axial member, said axial member being able to translate along a length of said channel;

an attachment member, said attachment member being connected to said axial support member;

a balancer, said balancer having a hook for connecting to said attachment member and a cable for attachment to a central support member, said cable including a slidable stop for adjusting said cable to a plurality of vertical positions;

a spreader bar, said spreader bar including a first support ring for attaching to said central support member, a second support ring for attaching to a first lateral support member and a third support ring for attaching to a second lateral support member, said first and second lateral support members each being attachable to a first and a second support ring; and a plurality of straps, said plurality of straps being attachable to said first and second support rings and to a radiation shielding garment, wherein an operator can attach said plurality of straps to said radiation shielding garment whereby a weight of said radiation shielding garment is substantially offset thereby allowing said operator substantially unbiased mobility along a transverse axis of said swing arm channel and around a 360 degree rotational axis of said vertical member.

11. The radiation shielding suspension device of claim 10, wherein said portable structure comprises a support stand, wherein said support member is mounted to said support stand.

12. The radiation shielding suspension device of claim 11, wherein said portable structure includes a plurality of wheels.

13. The radiation shielding suspension device of claim 12, further including a plurality of wheel locks.

14. The radiation shielding suspension device of claim 11, wherein said portable structure comprises a base, a vertical support post, a horizontal support post, a support brace, and a mounting pad for mounting said support member.

15. The radiation shielding suspension device of claim 10, wherein said plurality of straps comprises hook and loop fasteners.

16. The radiation shielding suspension device of claim 10, wherein said plurality of straps is two straps, said straps each being attachable to a shoulder area of said radiation shielding garment.

17. The radiation shielding suspension device of claim 10, wherein said balancer is a spring type tool balancer.

18. The radiation shielding suspension device of claim 10, wherein said radiation shielding garment is a lead apron.

19. A method of preventing injury to an operator while wearing a radiation shielding garment comprising:

a. attaching a suspension device to a structure, said device comprising a support member including at least one aperture for mounting said support member to said structure; a vertical member, said vertical member being fixedly attached to said support member and being substantially perpendicular to said vertical member; a swing arm, said swing arm being rotationally attached to said vertical member, said swing arm including a stop for fixing said swing arm at a plurality of vertical positions on said vertical member, and a channel, said channel including an axial member, said axial member being able to translate along a length of said channel; an attachment member, said attachment member being connected to said axial support member; a balancer, said balancer having a hook for connecting to said attachment member and a cable for attachment to a central support member, said cable including a slidable stop for adjusting said cable to a plurality of vertical positions; a spreader bar, said spreader bar including a first support ring for attaching to said central support member, a second support ring for attaching to a first lateral support member and a third support ring for attaching to a second lateral support member, said first and second lateral support members each being attachable to a first and a second support ring; and a plurality of straps, said at plurality of straps being attachable to said first and second support rings and to said radiation shielding garment;

b. attaching said plurality of straps to said radiation shielding garment whereby a weight of said radiation shielding garment is substantially offset thereby allowing said operator substantially unbiased mobility along a transverse axis of said swing arm channel and around a 360 degree rotational axis of said vertical member.

20. The method of claim 19, wherein said structure is a portable structure.

\* \* \* \* \*